(12) United States Patent
Bengtsson et al.

(10) Patent No.: US 9,889,258 B2
(45) Date of Patent: Feb. 13, 2018

(54) DRUG FILLED DELIVERY ASSEMBLY

(71) Applicant: Novo Nordisk A/S, Bagsvaerd (DK)

(72) Inventors: Henrik Bengtsson, Taastrup (DK); Jonas K. Pedersen, Frederiksberg (DK); Rikke B. Andersen, Copenhagen V (DK); Jeppe Sturis, Vaerloese (DK); Kezia A. Juul, Copenhagen N (DK); Lars Eilertsen, Fredensborg (DK); Ulla Ribel-Madsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 778 days.

(21) Appl. No.: 14/361,527

(22) PCT Filed: Nov. 30, 2012

(86) PCT No.: PCT/EP2012/074071
§ 371 (c)(1),
(2) Date: May 29, 2014

(87) PCT Pub. No.: WO2013/079652
PCT Pub. Date: Jun. 6, 2013

(65) Prior Publication Data
US 2014/0336586 A1 Nov. 13, 2014

Related U.S. Application Data

(60) Provisional application No. 61/567,779, filed on Dec. 7, 2011.

(30) Foreign Application Priority Data

Dec. 1, 2011 (EP) .................................... 11191500

(51) Int. Cl.
*A61M 5/24* (2006.01)
*A61M 5/20* (2006.01)
(Continued)

(52) U.S. Cl.
CPC ............ *A61M 5/24* (2013.01); *A61M 5/2033* (2013.01); *A61M 5/2466* (2013.01);
(Continued)

(58) Field of Classification Search
CPC .... A61M 5/19; A61M 5/2448; A61M 5/2455; A61M 5/2459; A61M 5/2466;
(Continued)

(56) References Cited

U.S. PATENT DOCUMENTS 2,283,234 A    5/1942  Smith
3,892,237 A *  7/1975  Steiner ................ A61M 5/2053
                                                     604/157

(Continued)

FOREIGN PATENT DOCUMENTS

EP          943349 A1   9/1999
JP       2008535636 A   9/2008
(Continued)

*Primary Examiner* — Kami A Bosworth
(74) *Attorney, Agent, or Firm* — Wesley Nicolas (57) ABSTRACT

A drug delivery assembly includes a housing (110), a piston (120) axially displaceable in the housing, and a variable volume reservoir (105) formed by the housing and the piston and containing a fluid first drug. The assembly further includes an exterior fluid inlet (150) arranged in or configured to be arranged in fluid communication with the reservoir, a fluid outlet (145) arranged in or configured to be arranged in fluid communication with the reservoir, biasing means (130) configured for moving the piston forwards, and releasable retaining means (113) configured for retaining the piston in an initial position, whereby the biasing means is allowed to move the piston forwards to expel fluid drug from the reservoir when the retaining means is released.

7 Claims, 7 Drawing Sheets

(51) Int. Cl.
*A61M 5/32* (2006.01)
*A61M 5/178* (2006.01)

(52) U.S. Cl.
CPC ... *A61M 5/3294* (2013.01); *A61M 2005/1787* (2013.01); *A61M 2005/2474* (2013.01)

(58) Field of Classification Search
CPC ...... A61M 5/281; A61M 5/284; A61M 5/285; A61M 5/286; A61M 5/288; A61M 5/31596; A61M 2005/2451; A61M 2005/247; A61M 2005/2474; A61M 2005/287
See application file for complete search history.

(56) References Cited

U.S. PATENT DOCUMENTS

| | | | |
|---|---|---|---|
| 3,911,916 A | | 10/1975 | Stevens |
| 4,424,057 A | * | 1/1984 | House ............... A61M 5/31596 604/88 |
| 4,643,721 A | * | 2/1987 | Brunet ............... A61M 5/2066 604/191 |
| 5,102,388 A | * | 4/1992 | Richmond ........ A61M 5/31596 604/191 |
| 5,637,087 A | * | 6/1997 | O'Neil ................. A61M 5/282 604/82 |
| 6,319,225 B1 | | 11/2001 | Sugita et al. |
| 6,723,074 B1 | | 4/2004 | Halseth |
| 7,645,264 B2 | | 1/2010 | Marsh et al. |
| 2003/0125676 A1 | | 7/2003 | Swenson et al. |
| 2004/0133163 A1 | | 7/2004 | Schiffmann |
| 2005/0075602 A1 | | 4/2005 | Cherif-Cheikh et al. |
| 2006/0229562 A1 | * | 10/2006 | Marsh ................... A61M 5/204 604/164.01 |
| 2013/0218089 A1 | * | 8/2013 | Davies ................ A61M 5/3294 604/191 |
| 2013/0226080 A1 | * | 8/2013 | Davies ................ A61M 5/2033 604/89 |
| 2013/0237922 A1 | * | 9/2013 | Davies ................ A61M 5/2425 604/205 |

FOREIGN PATENT DOCUMENTS

| | | |
|---|---|---|
| JP | 2013538636 A | 10/2013 |
| JP | 2013542023 A | 11/2013 |
| JP | 2013542797 A | 11/2013 |
| WO | 2010033806 A2 | 3/2010 |
| WO | 2010/139666 A1 | 12/2010 |
| WO | 2010/139671 A1 | 12/2010 |
| WO | 2010139676 A1 | 12/2010 |
| WO | 2011095478 A1 | 8/2011 |
| WO | 2011095480 A1 | 8/2011 |
| WO | 2011095483 A1 | 8/2011 |
| WO | 2011095486 A1 | 8/2011 |
| WO | 2011095488 A1 | 8/2011 |
| WO | 2011095489 A1 | 8/2011 |
| WO | 2011117284 A1 | 9/2011 |
| WO | 2011117287 A1 | 9/2011 |

* cited by examiner

DRUG FILLED DELIVERY ASSEMBLY

CROSS-REFERENCE TO RELATED APPLICATIONS

This application is a 35 U.S.C. § 371 National Stage application of International Application PCT/EP2012/074071 (published as WO 2013/079652), filed Nov. 30, 2012, which claimed priority of European Patent Application 11191500.5, filed Dec. 1, 2011; this application claims priority under 35 U.S.C. § 119 of U.S. Provisional Application 61/567,779; filed Dec. 7, 2011.

The present invention generally relates to a drug filled delivery assembly adapted to be used in combination with a drug delivery device. In specific embodiments the invention relates to a drug delivery system configured to deliver more than one kind of drug through a common dispense interface.

BACKGROUND OF THE INVENTION

In the disclosure of the present invention reference is mostly made to the treatment of diabetes, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

For some diseases and/or some disease states optimal treatment may require the administration of more than one type of drug. For example, it may be beneficial to treat a diabetic person with subcutaneous administration of both a long acting insulin formulation and a GLP-1 (glucagon-like peptide-1) based drug formulation, e.g. a GLP-1 analogue such as liraglutide marketed as Victoza® or exenatide marketed as Byetta® or as Bydureon® in its long-acting form.

There are a number of potential problems when delivering two active drug substances simultaneously. For a combined liquid formulation the two drug substances may interact with each other during long-term, shelf life storage. Therefore, it may be advantageous to store the active components separately and only combine them at the point of delivery, e.g. by injection, needle-less injection, pumps, or inhalation. However, the process for administering the two agents needs to be simple and convenient for the user to perform reliably, repeatedly and safely.

A further problem is that the amount for each drug substance making up the combination therapy may need to be varied for each user or at different stages of their therapy. For example, one or more drugs may require a titration period to gradually introduce a patient to a correct dose. A further example would be if one drug requires a non-adjustable fixed dose while the other is varied in response to a patient's symptoms or physical condition. This problem means that pre-mixed formulations of multiple active drug substances may not be suitable as these pre-mixed formulations would have a fixed ratio of the active components, which could not be varied by the healthcare professional or user.

Additional problems may arise where a multi-drug therapy is required, because many users may have difficulties when having to use more than one drug delivery system or make the necessary accurate calculation of the required dose combination. Addressing this issue fixed-dose medicated modules adapted to be mounted on variable-dose delivery devices have been proposed, see e.g. WO 2011/117284 and WO 2011/117287.

Having regard to the above, it is an object of the present invention to provide systems and devices which are configured to help a user in the administration of two or more drugs in an efficient, simple, safe and reliable way. It is a further object to provide a fluid delivery device comprising a first drug, the device allowing a further drug to be administered through a common fluid outlet, this in an efficient, simple, safe and reliable way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect of the invention a drug delivery assembly is provided comprising a housing, a piston axially displaceable in the housing, and a variable volume reservoir formed by the housing and the piston and in an initial state containing a fluid first drug. The assembly further comprises an exterior fluid inlet arranged in or configured to be arranged in fluid communication with the reservoir, a fluid outlet arranged in or configured to be arranged in fluid communication with the reservoir, biasing means for moving the piston forwards, and releasable retaining means for retaining the biasing means in an energized state, whereby the biasing means is allowed to move the piston forwards to expel fluid drug from the reservoir when the retaining means is released. By "exterior" a fluid inlet is defined which is configured to be arranged in fluid communication with an external fluid supply.

In this way the fluid inlet may be arranged in fluid communication with a fluid outlet of a drug delivery device comprising a second fluid drug, this allowing the two drugs to be expelled through the fluid outlet of the drug delivery assembly which thereby serves as a common fluid outlet for the two drugs. Correspondingly, separate storage reservoirs for two or more active drugs can be combined and the drugs delivered to the patient during a single delivery procedure. Further, by providing a variable volume reservoir it is possible to avoid that the first drug merely is replaced by the second drug, this providing greater dosing accuracy for the second drug. The retaining means may serve to retain the piston in its initial position by e.g. preventing the piston from being moved or by retaining the biasing means acting on the piston in an initial energized state.

Thus setting a dose of one drug does not automatically fix or determines the dose of the other drug (i.e. the non-user settable drug). Moreover, the opportunity may be given for varying the quantity of one or both drugs. For example, one fluid quantity can be varied by changing the properties of the injection device (e.g. dialling a user variable dose or changing the device's "fixed" dose). The second fluid quantity can be changed by manufacturing a variety of secondary drug containing assemblies with each variant containing a different volume and/or concentration of the second drug. The user or healthcare professional would then select the most appropriate secondary assembly or series of different assemblies for a particular treatment regime.

The biasing means may be configured to be actuated from an initial state to an energized state by a user operation. The biasing means may e.g. be in the form of a spring which in its initial state may be slightly compressed, e.g. to prevent rattle, however, in contrast to the energized state the energy stored in the initial state is not sufficient to fully empty the reservoir. Alternatively, the assembly may be provided with pre-energized biasing means.

The drug delivery assembly may be configured to be attached to a drug delivery device comprising a second reservoir containing a second fluid drug, and coupling means configured for attachment to corresponding coupling means arranged on the drug delivery assembly, wherein, when the coupling means are attached to each other, the fluid inlet is arranged in fluid communication with the second reservoir and the biasing means is actuated from the initial state to the energized state. Alternatively the biasing means may be actuated by separate means.

In an exemplary embodiment of the drug delivery assembly, the fluid outlet has an initial state in which there is no fluid communication between the fluid outlet and the reservoir, and an actuated state in which there is fluid communication between the fluid outlet and the reservoir, this allowing the energized biasing means to move the piston forwards to expel fluid drug from the reservoir through the fluid outlet.

To allow a controlled flow of fluid through the assembly, the fluid inlet has an initial state in which there is no fluid communication between the fluid inlet and the reservoir, and an actuated state in which there is fluid communication between the fluid inlet and the fluid outlet. To provide the fluid communication, the piston comprises a fluid conduit (e.g. a bore) in flow communication with the fluid inlet, the piston being moveable from the initial position in which there is no fluid communication between the fluid conduit and the fluid outlet and to a connected position in which a fluid communication is provided between the fluid outlet and the fluid conduit and thereby between the fluid inlet and the fluid outlet.

The reservoir may comprise a needle penetrable area and the fluid outlet may be in the form of a distal hollow needle axially displaceable between an initial position in which there is no fluid communication between the fluid outlet and the reservoir, and an actuated position in which the distal hollow needle is arranged through the needle penetrable area and thereby in fluid communication with the reservoir, whereby the biasing means in an energized state is allowed to move the piston forwards to expel fluid drug from the reservoir through the distal hollow needle.

The proximal portion of the distal hollow needle may in its actuated position project into the reservoir, and the piston may comprise a needle penetrable area. The fluid inlet may be in the form of a proximal hollow needle having a distal portion arranged in the piston conduit and being in flow communication therewith as the piston is moved axially from its initial position to its connected position in which the proximal portion of the distal hollow needle is arranged through the piston needle penetrable area and thereby in flow communication with the proximal hollow needle. By this arrangement a fluid communication can be provided between the distal and proximal hollow needle via the piston conduit.

In a further aspect of the invention a medical assembly is provided comprising a drug delivery assembly as described above in combination with a drug delivery device comprising a second reservoir containing a second fluid drug, an expelling assembly for expelling a dose of drug from the second reservoir, and coupling means. The drug delivery assembly further comprises corresponding coupling means configured for attachment to the device coupling means, such that, when the coupling means are attached to each other, the fluid inlet is arranged in fluid communication with the second reservoir.

In a further exemplary embodiment the retaining means is configured to be released when a fluid is introduced via the fluid inlet into the reservoir, this allowing the biasing means to be released when the piston is moved backwards by fluid introduced into the reservoir via the fluid inlet.

The drug delivery assembly may further comprise a hollow needle having a proximal end providing the fluid inlet, a distal end providing the fluid outlet, and an intermediate opening arranged or configured to be arranged in fluid communication with the reservoir. The hollow needle may be arranged through the piston with a seal being provided between the piston and the hollow needle, this allowing the piston to move axially backwards (proximally) and forwards (distally) relative to the hollow needle. The hollow needle may be arranged to have an initial position and an actuated position, the intermediate opening being arranged in sealed engagement with the piston when in the initial position, and in fluid communication with the reservoir when in the actuated position.

The drug delivery assembly may be configured to be attached to a drug delivery device comprising a second reservoir containing a second fluid drug, wherein the drug delivery device comprises second coupling means, and the drug delivery assembly comprises first coupling means configured for attachment to the second coupling means. When the first and second coupling means are attached to each other, the fluid inlet is arranged in fluid communication with the second reservoir and the hollow needle is moved to its actuated position, whereby a fluid communication is established between the second reservoir and the drug delivery assembly reservoir as well as between the drug delivery assembly reservoir and the fluid outlet. A one-way valve preventing a flow of fluid from the reservoir to the fluid inlet may be provided.

In a further aspect of the invention a medical assembly is provided comprising a drug delivery assembly of the above-described type having an actuatable hollow needle, and a drug delivery device comprising a second reservoir containing a second fluid drug, an expelling assembly for expelling a dose of drug from the second reservoir and comprising spring means for driving the expelling assembly, as well as second coupling means. The drug delivery assembly further comprises first coupling means configured for attachment to the second coupling means, such that, when the first and second coupling means are attached to each other, the fluid inlet is arranged in fluid communication with the second reservoir and the hollow needle is moved to its actuated position, whereby a fluid communication is established between the second reservoir and the drug delivery assembly reservoir as well as between the drug delivery assembly reservoir and the fluid outlet, and wherein the biasing means is configured to provide a first pressure in the drug delivery assembly reservoir and the spring means is configured to provide a second higher pressure in the second reservoir, this preventing a flow of fluid from the drug delivery assembly reservoir to the fluid inlet.

Alternatively, the spring means may be configured to provide a second lower pressure in the second reservoir, whereby initially the piston will move forwards until the drug has been fully expelled from the assembly reservoir and delivered via the needle after which drug will be expelled from the cartridge. Indeed, this may require that drug is not allowed to flow rearwards from the assembly reservoir and into the cartridge via the intermediate opening. One way of preventing this would be to rely on the delivery device being provided with one-way means preventing a flow of fluid from the reservoir to the fluid inlet, e.g. by a unidirectional coupling preventing the piston rod from being pushed back, e.g. as in FlexTouch® from Novo Nordisk. The delivery assembly may alternatively be provided with a one-way valve preventing a flow of fluid from the reservoir to the fluid inlet.

In a further exemplary embodiment the reservoir in the initial state is pressurized by the biasing means. The fluid outlet has an initial state in which there is no fluid communication between the fluid outlet and the reservoir, and an actuated state in which there is fluid communication between the fluid outlet and the reservoir, thereby allowing the biasing means to move the piston forwards to expel fluid drug from the reservoir through the fluid outlet, and the fluid inlet has an initial state in which there is no fluid communication between the fluid inlet and the reservoir, and an actuated state in which there is fluid communication between the fluid inlet and the fluid outlet. The fluid outlet may be coupled to a trigger member having a surface portion adapted to be placed against a skin surface and being moveable relative to the housing, this allowing the fluid outlet to be moved to an actuated position in fluid communication with the reservoir when the trigger member is placed against a skin surface of a user.

The piston may be provided with a fluid conduit in flow communication with the fluid inlet, the piston being moveable from the initial position in which there is no fluid communication between the fluid conduit and the fluid outlet and to a connected position in which a fluid communication is provided between the fluid outlet and the fluid conduit and thereby between the fluid inlet and the fluid outlet via the fluid conduit.

The reservoir may be provided with a needle penetrable area and the fluid outlet may be in the form of a distal hollow needle displaceable between an initial position in which there is no fluid communication between the fluid outlet and the reservoir, and an actuated position in which the distal hollow needle is arranged through the needle penetrable area and thereby in fluid communication with the reservoir. The proximal portion of the distal hollow needle may be arranged to in its actuated position to project into the reservoir with the piston comprising a needle penetrable area. The fluid inlet may be in the form of a proximal hollow needle having a distal portion arranged in the piston conduit and being in flow communication therewith as the piston is moved axially from its initial position to its connected position in which the proximal portion of the distal hollow needle is arranged through the piston needle penetrable area and thereby in flow communication with the proximal hollow needle.

In a further aspect the delivery assembly comprises user actuatable release means configured to release the retaining means when actuated. The user actuatable release means may comprise a slideable needle guard covering the distal needle in the initial state, the needle guard being pushed proximally when the assembly is placed against a skin surface by the user. The needle guard may be spring-biased such that it automatically is moved distally to cover the distal needle when the assembly is withdrawn from the skin surface. The needle guard could also be used to provide a lock such that the assembly cannot be released until the guard has been pushed proximally. For a design comprising to the above-described actuated needle feature this would allow a user to perform a delivery device "air shot", i.e. to purge air from the needle before inserting the distal needle subcutaneously.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs. Correspondingly, the term "subcutaneous" delivery is meant to encompass any method of transcutaneous delivery to a subject.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

Figure 1:
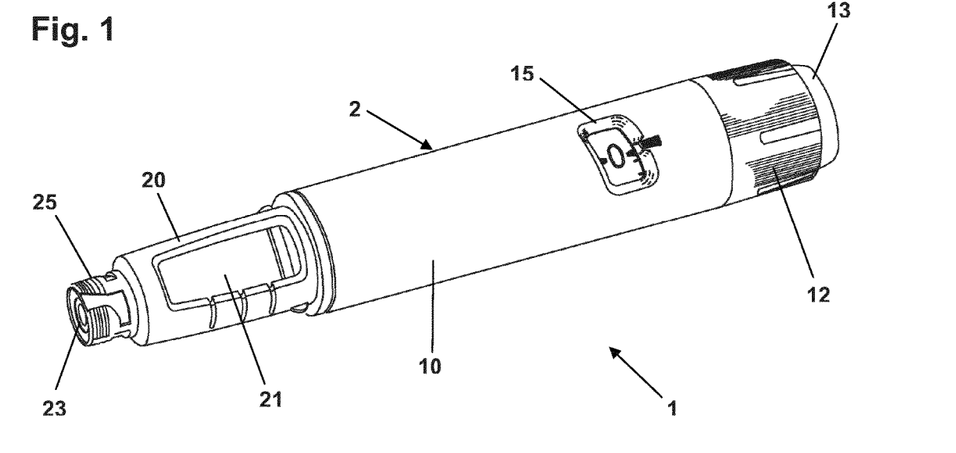
FIG. 1 shows an embodiment of a drug delivery device.

Referring to FIG. 1 a pen-formed drug delivery device 1 will be described. The device represents a "generic" drug delivery device providing an example of a device in combination with which embodiments of the present invention is intended to be used. More specifically, the pen device comprises a cap part (not shown) and a main part 2 having a proximal portion 10 in which a drug expelling mechanism is arranged, and a distal reservoir portion 20 in which a drug-filled transparent cartridge 21 with a distal needle-penetratable septum 23 is arranged and hold in place by a cartridge holder 22 mounted to the proximal portion, the cartridge holder having openings allowing a portion of the cartridge to be inspected. The device may be disposable and come with a pre-mounted cartridge which is not intended to be removed, or it may be designed to be loaded with a new cartridge by the user. The cartridge is provided with a piston driven by a piston rod forming part of the expelling mechanism. A proximal-most rotatable dose ring member 12 serves to manually set a desired dose of drug shown in display window 15 and which can then be expelled when the release button 13 is actuated. Depending on the type of drug delivery device, the expelling mechanism may comprise a spring which is strained during dose setting and then released to drive the piston rod when the release button 13 is actuated. Alternatively the expelling mechanism may be fully manual in which case the dose ring member 12 and the release button 13 moves proximally during dose setting corresponding to the set dose size, and then moved distally by the user to expel the set dose. The cartridge (or alternatively the cartridge holder) is provided with distal coupling means in the form of a needle hub mount 25 having, in the shown example, an external thread as well as a bayonet adapted to engage an inner thread or a bayonet of a corresponding hub of a needle assembly (see below). When using a drug delivery device of the above general type (which may have other form-factors and also be provided with a motorized expelling mechanism), the user is typically recommended to take a subcutaneous injection by performing the following steps: remove the cap to uncover the needle mount, mount a new needle assembly, set a dose amount to be expelled by rotating the dose setting member, when the needle has been inserted subcutaneously actuate the release means for driving or releasing the drug expelling means to expel the set dose, after having withdrawn the needle from the skin remove the needle assembly from the needle mount, and re-attach the cap to cover the needle mount.

Figure 2:
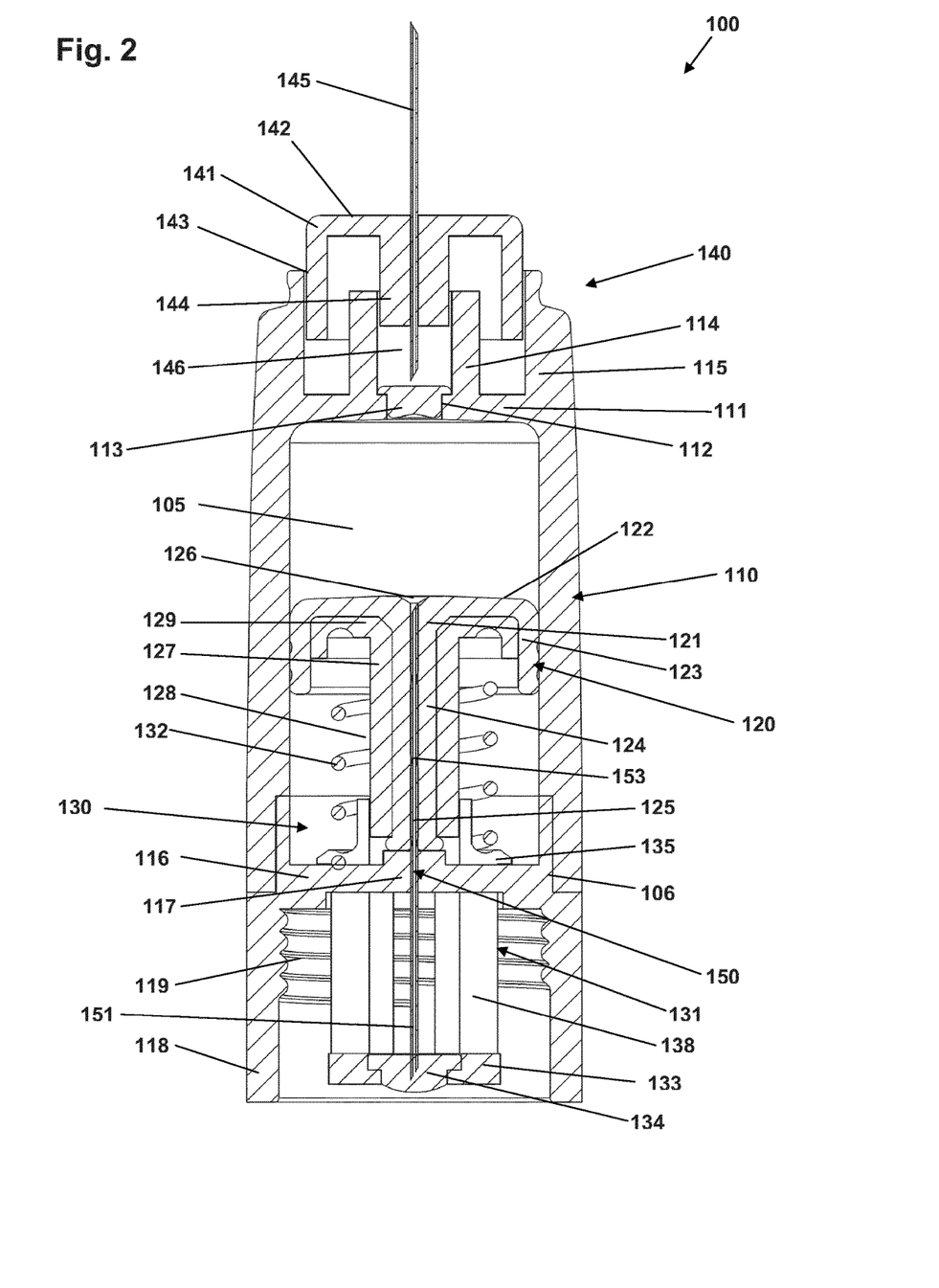
FIG. 2 shows a cross-sectional view of a first embodiment of a pre-filled delivery assembly.

FIG. 2 shows schematically in an initial state a first embodiment of a pre-filled delivery assembly 100 comprising a housing 110, a piston assembly 120, a drive assembly 130, a distal needle assembly 140 and a proximal hollow needle 150. The generally cylindrical housing 110 defines a general axis for the assembly and comprises a distal wall portion 111 having a central opening 112 in which a needle penetrable reservoir septum 113 is arranged, a distally extending tubular portion 114 arranged around the central opening, a distally extending outer skirt portion 115, a proximal wall portion 116 having a central opening 117 around which four quarter-circle openings are arranged (see FIG. 5B), and a proximally extending skirt portion 118 provided on the inner surface with circumferential coupling means 119 (e.g. an inner thread as shown or a bayonet) allowing the assembly to be mounted on a corresponding hub mount of a drug delivery device, e.g. as shown in FIG. 1. Between the two wall portions an interior cavity 105 is provided which in an initial sealed state is filled with a liquid drug formulation. The shown housing is assembled from two parts corresponding to a circumferential division 106 arranged between the two wall portions, this allowing components to be mounted in the cavity during assembly.

The piston assembly 120 is axially displaceable arranged in the cavity and comprises in the shown embodiment a first part 121 and a supporting second part 127, however, the piston could also be manufactured as a single element. The first part comprises a disc portion with a distally facing piston surface 122 and a proximally extending circumferential skirt portion 123 in sliding and sealed engagement with an interior wall portion of the housing, a variable volume reservoir being formed between the distal wall portion, the piston surface and the housing. The first part further comprises a proximally extending bore portion 124 having an axial bore 125 with a proximal and a distal opening and a number of circumferential constrictions 153, a needle penetrable piston septum 126 being arranged in the distal portion. The second part comprises a cylindrical stem portion 128 surrounding and engaging the bore portion as well as a distal circumferential flange portion 129 engaging and supporting the piston disc.

Figure 4A:
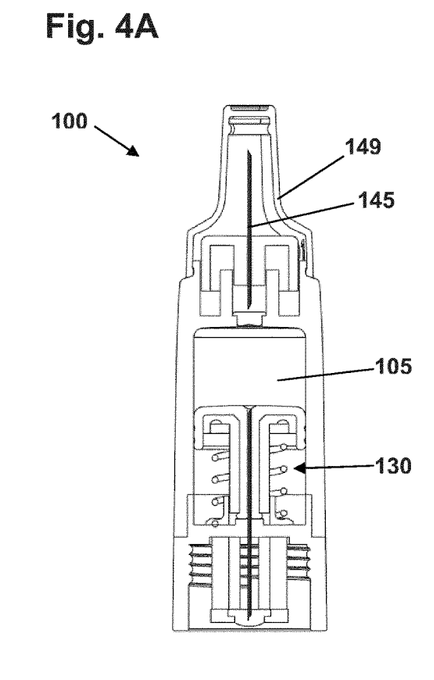
Figure 4B:
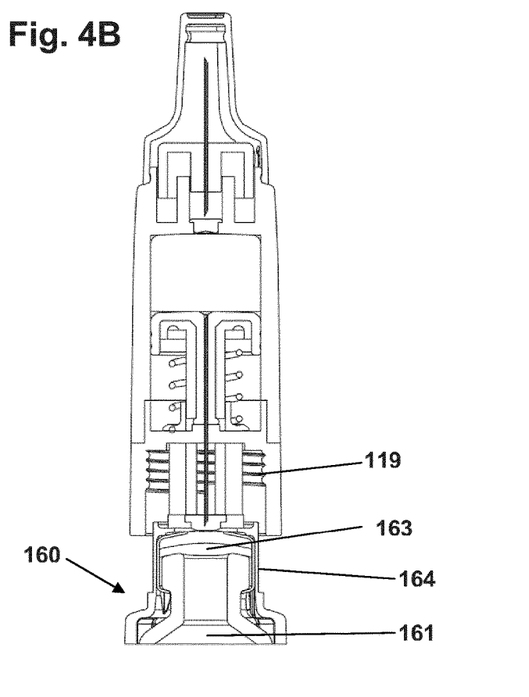
Figure 4C:
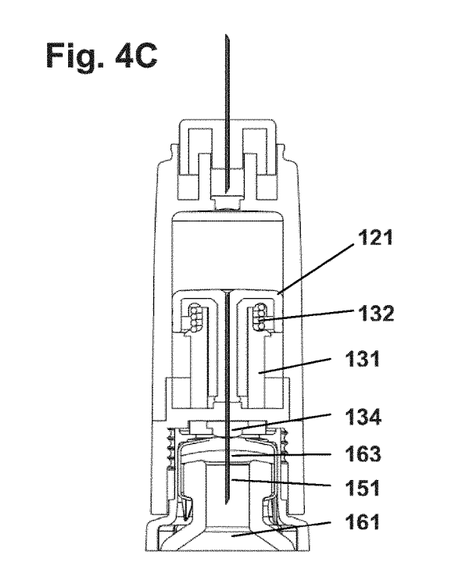

The drive assembly 130 comprises a spring loader member 131 and a helical coil spring 132. The spring loader member comprises a proximal disc portion 133 with a central opening in which a needle penetrable proximal septum 134 is arranged, as well as four distally extending legs 138 each having a general quarter-circle form, the interior surface of the legs being in sliding and supporting engagement with the cylindrical stem portion 128. The distal portion of each leg comprises a laterally extending flange 135 also having a general quarter-circle form. In the initial state as shown in FIG. 4A the disc portion 133 is arranged at a distance from the proximal wall with the four legs extending distally through the corresponding four quarter-circle openings in the proximal wall portion. As the flanges 135 extend laterally relative to the openings the proximal-facing surface of the flanges abut the proximal wall, this securing the spring loader member relative to the housing yet allows it to move distally. The coil spring 122 is arranged concentrically around the stem portion with the distal end being supported by the piston flange portion and the proximal portion being supported by the leg flanges. In the initial state the spring is under light compression which, as the piston cannot move distally due to liquid filled sealed reservoir, provides a proximally directed force securing the spring loader member in its proximal-most initial position.

The proximal hollow needle 150 is fixedly arranged in the proximal wall portion central opening 116 and comprises a proximal portion 151 (often termed "back needle") adapted to penetrate a cartridge septum of a drug delivery device when the assembly is mounted thereto, however, in the initial position the proximal end of the needle is closed by the proximal septum 134. The distal portion 152 of the proximal hollow needle is sealingly received in the piston bore by means of the interior constrictions 153 (alternatively an elastomeric seal member may be arranged at the proximal end of the bore) and thus in sealed fluid communication therewith during the pistons axial travel from its initial proximal position and its fully actuated distal position (see below), the piston septum 126 initially providing a barrier between the interior of the proximal hollow needle and the interior of the reservoir.

The distal needle assembly 140 comprises a needle carrier 141 with a distally facing contact surface 142 adapted to engage a skin surface of a user, a proximally extending circumferential skirt portion 143 in sliding and frictional engagement with the outer skirt portion 115, a proximally extending stem portion 144 in sliding and frictional engagement with the tubular portion 114 and comprising a central bore in which a distal hollow needle 145 is fixedly arranged, the needle comprising a proximal portion 146 adapted to penetrate the reservoir septum 113 and protrude into the reservoir, however, in the initial position the proximal end of the needle is positioned distally of the septum. A needle cover 149 (see FIG. 4A) is initially attached to the distal end of the housing to cover the needle and needle carrier.

In the embodiment of FIG. 2 the housing is made from a polymeric material (or provided with a coating) allowing an inner surface portion of the housing to be in contact with a liquid drug formulation for a period corresponding to the intended shelf live for the assembly. Alternatively the housing may be made fully or in part from glass. Correspondingly, FIG. 3 shows an alternative embodiment in which the housing 110 has been replaced with a glass vial as well as modified front and rear housing portions.

Figure 3:
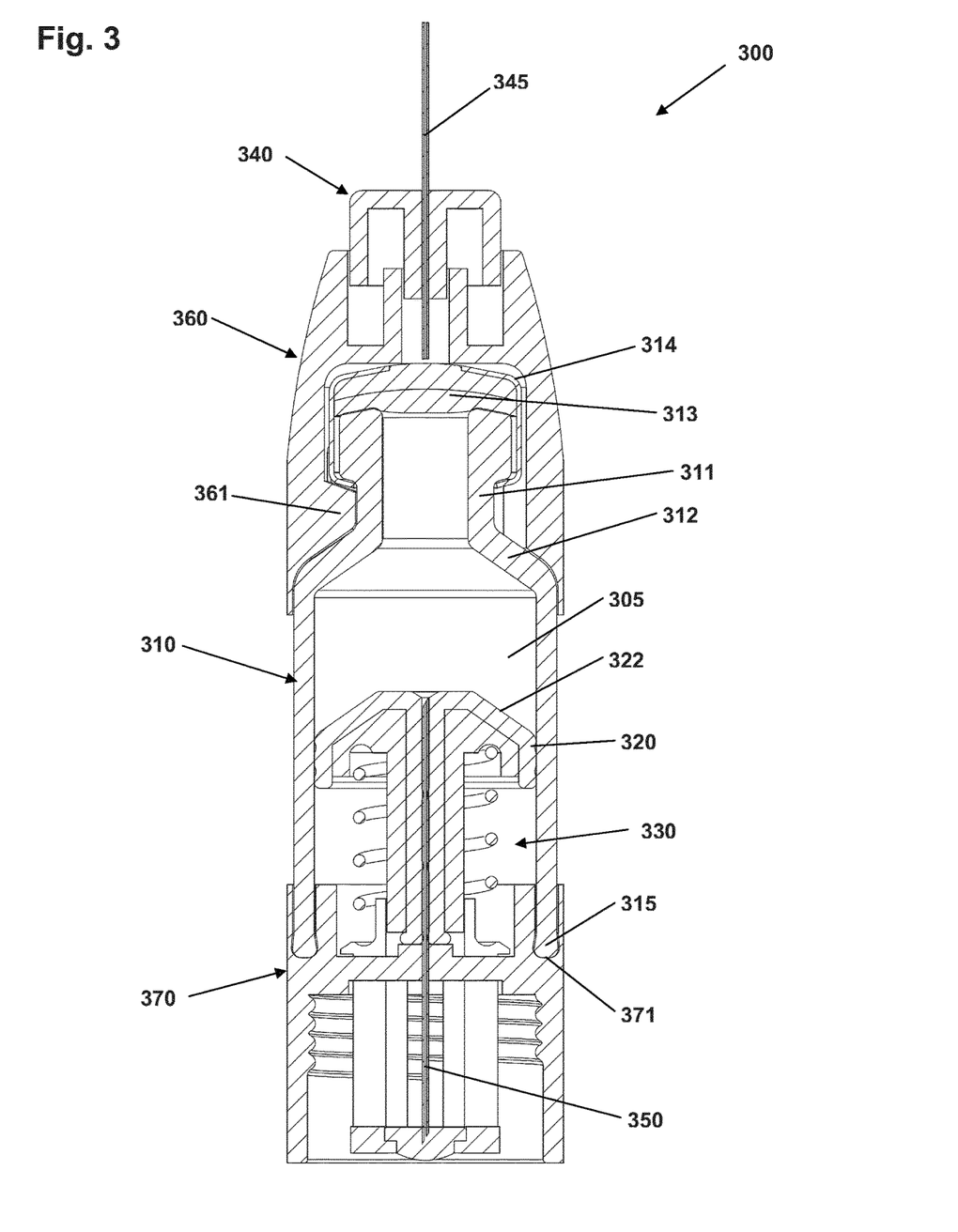
FIG. 3 shows in cross-section an alternative for the embodiment of FIG. 2, FIGS. 4A-4F show the embodiment of FIG. 2 in different states of use, FIGS. 5A and 5B corresponds to FIGS. 4A and 4C in a different view.

More specifically, FIG. 3 shows a drug delivery assembly 300 comprising a glass vial 310 with a piston 320, a front part 360 and a rear part 370, the front and rear parts providing the glass vial with the structures and functionalities of the distal and proximal portions of the housing 110 of the FIG. 2 embodiment. Apart from the modified piston and the portions of the front and rear parts interfacing with the glass vial, the assembly of FIG. 3 is functionally identical with the assembly of FIG. 2.

The glass vial comprises a main cylindrical portion, a neck portion 311 with an outlet opening, a transitional shoulder portion 312 there between, a needle penetrable septum 313 and a circumferential holding member 314 for holding the septum in sealed engagement with the neck portion. The piston 320 has a distal surface 322 adapted to be accommodated in the shoulder portion, this reducing the dead space when the piston has been fully moved forwards to only the volume of the neck portion. The front part 360 comprises a proximal bore adapted to be mounted on the vial neck portion, the bore being provided with a protrusion 361 adapted to engage the vial between the holding member and the shoulder portion. The rear part 370 comprises a circumferential distal groove 371 adapted to engage and grip the circumferential rear edge of the glass vial.

With reference to FIGS. 2 and 4A-4F use of the drug-filled delivery assembly 100 in combination with a drug delivery device 160 of the type shown in FIG. 1 comprising a drug-filled cartridge 161 with a needle penetrable septum 163, a hub mount 164 and provided with a spring-driven expelling assembly will be described, however, the device may be of any suitable type, e.g. manual, spring or motor driven. In an exemplary embodiment the delivery assembly comprises a (first) reservoir 105 containing a first drug in the form of a GLP-1 formulation, and the cartridge (representing a second reservoir) contains a second drug in the form of an insulin formulation.

Figure 5A:
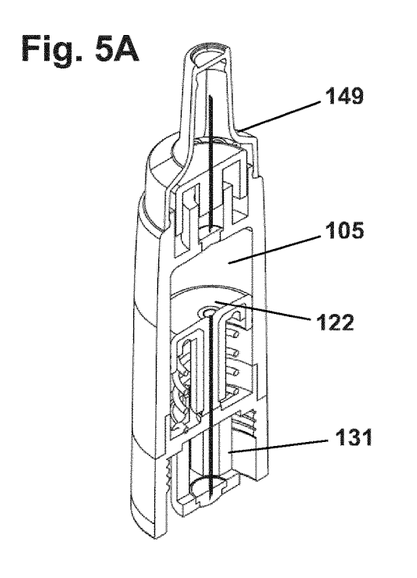
Figure 5B:
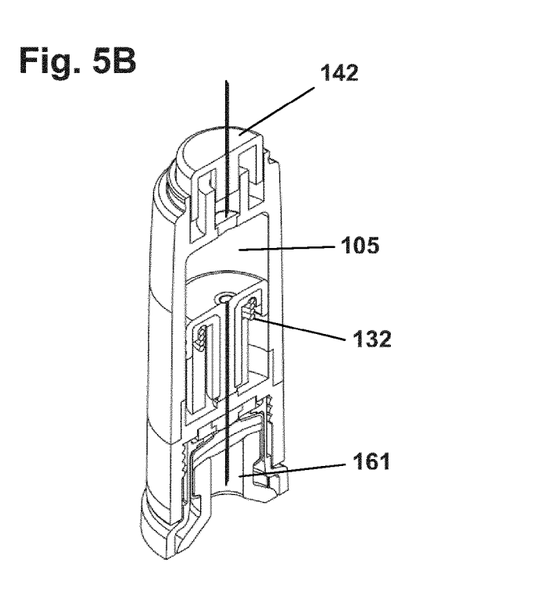

FIGS. 4A and 5A show the assembly 100 in its initial state with the needle cover 149 attached and the drive assembly 130 in a substantially non-energized state, the distal opening of the proximal hollow needle 150 positioned and sealed inside the piston bore, and the proximal opening of the distal hollow needle 145 positioned at a distance from the reservoir septum thereby providing a sealed drug reservoir.

The user then aligns the delivery assembly relative to the delivery device hub mount 164 (see FIG. 4B), mounts the assembly on the device, e.g. by means of the shown thread or alternatively by means of a bayonet coupling, and removes the needle cover. For illustrative purposes the device coupling means is not shown. As can be seen, when the assembly is mounted on the device via coupling means 119 engaging the hub mount 164, the back needle 151 penetrates the proximal septum 134 and is inserted through the septum 163 and into fluid communication with the interior of cartridge 161, and the spring loader member 131 is moved distally to thereby compress the spring 132 against the at this stage stationary piston 121 held in place by the retaining means, this energizing the spring and pressurizing the reservoir. At this stage the user may release the spring-driven expelling assembly of the delivery device, however, as the distal outlet of the proximal needle is sealed inside the piston bore, no drug will be expelled from the delivery device at this stage, see FIGS. 4C and 5B.

Figure 4D:
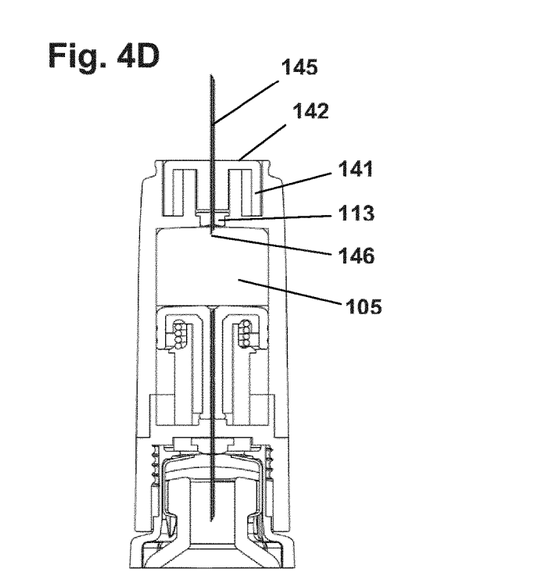
Figure 4E:
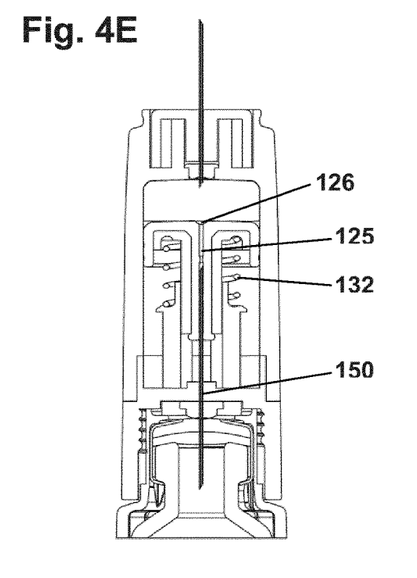

As the next step the user places the distal contact surface 142 of the assembly against a skin surface with a gentle force, whereby the pointed distal end of the distal needle 145 is inserted subcutaneously and the needle carrier 141 is moved proximally relative to the assembly housing, thereby inserting the proximal portion 146 of the needle through the reservoir septum 113 to establish a fluid communication with the reservoir 105 (see FIG. 4D). As the reservoir septum is punctured the piston retaining means is released and the piston starts to move distally by the expanding spring 132 thereby expelling drug from the assembly reservoir (see FIG. 4E). At this stage the distal outlet of the proximal needle 150 is still sealed inside the piston bore 125, however, if the drug in the device cartridge is pressurized at this point in time, then this pressure will also act on the piston, however, due to the area of the bore only to a very small extent.

Figure 4F:
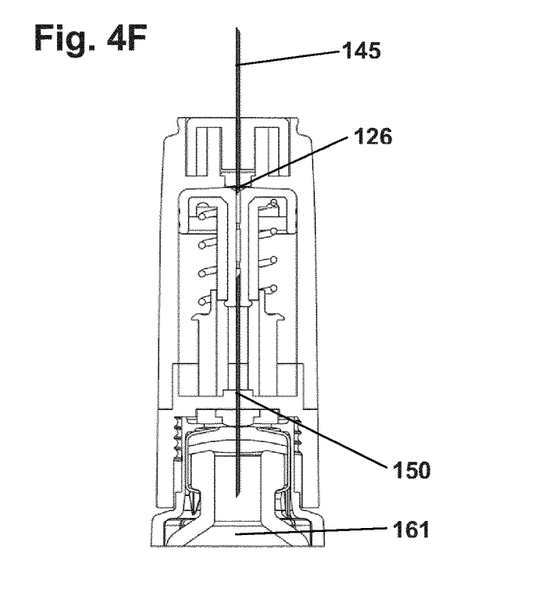

As the piston has been moved substantially to its distal-most position and the reservoir has ideally been fully emptied the proximal end of distal needle 145 projecting into the reservoir penetrates the piston septum 126 whereby a fluid communication is established between the distal needle 145 and the device reservoir 161 via the piston bore and the proximal needle (see FIG. 4F). As appears, the releasable retaining means for holding the spring in an energized state is provided in combination by the piston septum and the axially moveable distal needle.

If the delivery device has been energized and released before actuation of the delivery assembly then the second drug will start to be expelled from the cartridge 161. On the other hand, if e.g. the delivery device is manual the user can now start injection manually, e.g. by pushing down an injection button. To indicate that the reservoir has been emptied the assembly may be provided with means producing an audible "click" sound.

In an alternative embodiment (not shown) the spring loader may be dispensed with and the assembly may be provided to the user with a pre-compressed spring and thus a pressurized reservoir. In a further alternative embodiment (not shown) the needle carrier (or "trigger member") may be spring-biased such that it automatically is moved distally and the needle thereby out of engagement with the reservoir septum to thereby stop infusion (either of the first or the second drug) when the assembly is withdrawn from the skin surface.

Figure 6A:
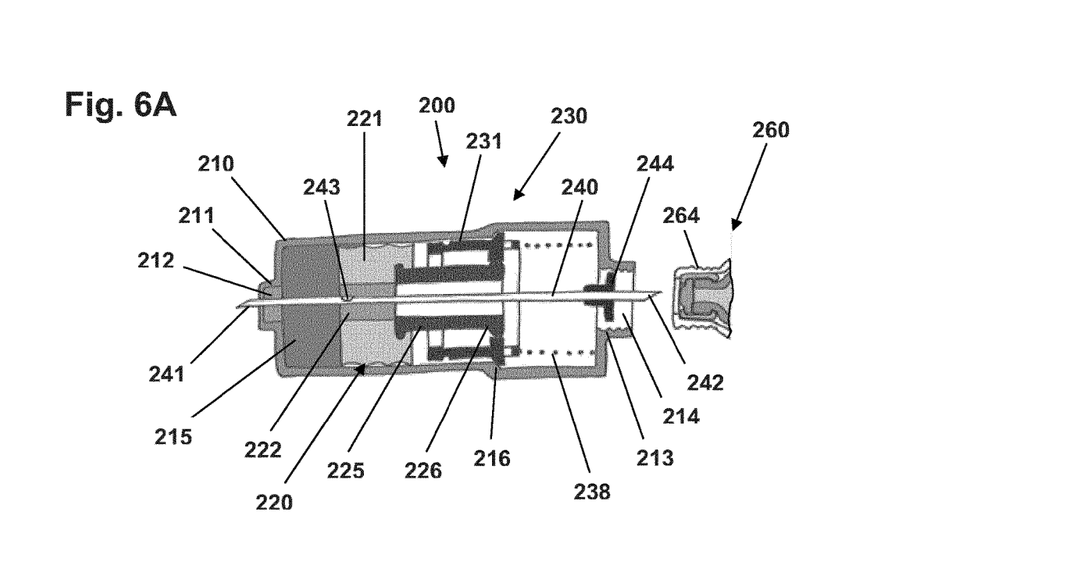
FIG. 6A shows a cross-sectional view of a second embodiment of a pre-filled delivery assembly.
Figure 6B:
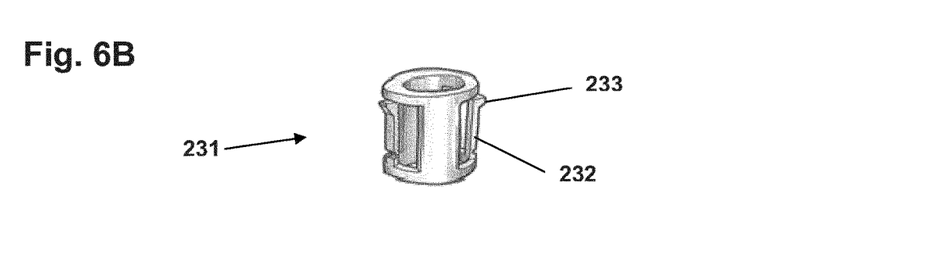
FIG. 6B shows an element of the second embodiment.

With reference to FIGS. 6A and 6B a second embodiment of a drug-filled delivery assembly 200 adapted to be used in combination with a drug delivery device 260 will be described, the assembly being shown in an initial state as supplied to the user.

The assembly comprises a housing 210, an axially displaceable piston 220, a drive assembly 230, and an axially displaceable hollow needle 240. In the shown embodiment the housing is made from a polymeric material (or provided with a coating) allowing an inner surface portion of the housing to be in contact with a liquid drug formulation for a period corresponding the intended shelf live for the assembly. Alternatively the housing may be made fully or in part from glass. The housing comprises a distal end portion 211 with a distal septum 212 comprising an axial bore trough which a pointed distal needle portion 241 is arranged and projects, and a proximal end comprising a tubular hub portion 213 provided with coupling means 214 (e.g. an inner thread as shown or a bayonet) allowing the assembly to be mounted on a corresponding hub mount, e.g. as shown in FIG. 1. In the shown embodiment a proximal pointed needle portion 242 initially projects from the hub portion. The piston 220 comprises a main portion 221 formed from a first elastomeric material providing a seal between the piston and an inner surface portion of the housing, and a central septum portion 222 formed from a second elastomeric material and with an axial bore through which the needle 240 is arranged in sliding and sealed engagement. Alternatively the piston may be formed from a single elastomeric material. A cylindrical release member 225 is attached to the piston and protrudes proximally therefrom, the release member comprising a circumferential proximal rim portion 226. When the piston is arranged in its initial position a reservoir 215 is formed between the piston and the housing, the reservoir being filled with a liquid drug formulation. The drive assembly 230 comprises a retaining member 231 and a biasing means in the form of a spring 238, the spring having a proximal end supported by the housing and a distal end exerting a force on the proximal end of the retaining member. The retaining member has a general tubular configuration with a distal end initially arranged at a distance from the proximal end surface of the piston main portion, the retaining member comprising two axially extending and opposed flexible locking arms 232 (see FIG. 6B) each having a free proximal end portion with a lateral protrusion 233 adapted to initially engage a proximal-facing support structure 216 arranged on the interior housing surface. In the shown embodiment the proximal-facing support structure 216 is in the form of an inner circumferential rim. The contact surfaces between the lateral protrusions and the support structure are axially inclined such that the spring force acting on the retaining member will result in an inwards directed force on the flexible arms, thereby forcing them out of engagement with the support. However, in the initial state the proximal rim portion 226 of the release member 225 is arranged to support the proximal ends of the flexible arms, thereby initially preventing the arms from disengaging their supports and the retaining member from being moved distally by the expanding spring. As appears, the retaining member, the release member and the support structure serve in combination as retaining means to initially retain the spring in an energized state. The hollow needle 240 comprises the above-described distal and proximal portions 241, 242, an intermediate opening 243 initially arranged in a closed and sealed position inside the piston septum member 222, as well as a proximal collar member 244 arranged in the vicinity of the tubular hub portion and adapted to engage a needle hub mount of a drug delivery device. The housing may be provided with stop structures (not shown) controlling distal travel of the needle collar member and proximal travel of the piston. The shown assembly 200 is supplied to the user in a sterile state enclosed in an outer container (not shown).

With reference to FIGS. 6A and 7A-7D use of the drug-filled delivery assembly 200 in combination with a drug delivery device 260 of the type shown in FIG. 1 comprising a drug-filled cartridge 261 and provided with a spring-driven expelling assembly will be described. In an exemplary embodiment the delivery assembly comprises a (first) reservoir 215 containing a first drug in the form of a GLP-1 formulation, and the cartridge (representing a second reservoir) contains a second drug in the form of an insulin formulation.

Figure 7A:
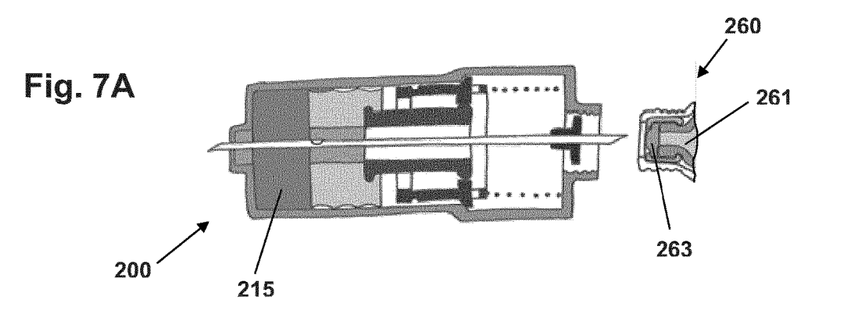
FIGS. 7A-7D show the embodiment of FIG. 6A in different states of use.

FIG. 7A shows the assembly 200 in an initial state with the drive assembly in its locked state and the needle intermediate opening 243 positioned and sealed inside the piston bore, thereby providing a sealed drug reservoir. A gap is provided between the piston and the retaining member.

When the assembly is attached to the hub mount 264 of the drug delivery device (either by a threaded coupling or a bayonet coupling) the proximal pointed end 242 of the hollow needle 240 is inserted through the cartridge septum 263. During the coupling action the distal end of the hub mount engages the needle collar member 244 thereby forcing the needle axially, whereby the intermediate opening 243 is moved out of engagement with the piston and positioned just proximally of the distal septum 212, this creating a fluid communication between the reservoir and the cartridge, between the reservoir and the distal needle portion, and thus a fluid communication between the cartridge and the distal needle portion, see FIG. 7B. At this point there will be substantially no flow of drug.

Figure 7B:
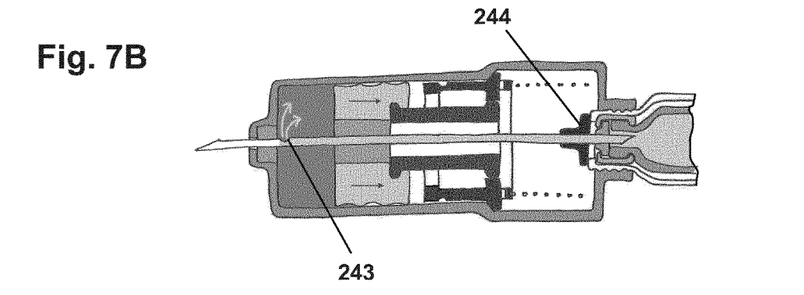

When the user has set the drug delivery device to a desired dose and thereby loaded the spring-driven expelling assembly the combined assembly (i.e. the drug-filled delivery assembly 200 and the drug delivery device) is ready for use. Correspondingly, when the user after having inserted the needle subcutaneously actuates the drug delivery device and thereby releases the spring, liquid drug is forced from the cartridge and through the hollow needle 240 and thereby out through both the intermediate opening 243 and the subcutaneously inserted distal end. However, as the opening is designed to have a flow resistance much smaller than the downstream portion of the hollow needle, most of the drug initially expelled from the cartridge will be forced into the reservoir and thus exert a proximally-directed force on the piston. As a consequence the piston including the release member 225 is moved proximally whereby the rim portion 226 is moved out of its supporting engagement with the locking arms 232. At the same time the proximal surface of the piston is moved into contact with the distal end of the retaining member. To prevent the retaining member and thus the piston from being moved further proximally the housing is provided with a protrusion (not shown) engaging the proximal end of the retaining member in its initial position. As described above, when the locking arms are no longer prevented from being moved inwards, the spring force acting on the retaining member will result in an inwards directed force on the flexible arms, thereby forcing them out of engagement with the support as the retaining member and thereby the piston are moved forwards by the spring 238 to thereby expel drug from the reservoir 215.

However, at the same time the piston is exposed to a proximally-directed pressure from the liquid in the reservoir corresponding to the pressure generated by the spring in the drug delivery device (less the pressure drop in the needle). If the force on the piston from the pressure in the reservoir generated by the device spring is higher than the force exerted on the piston from the assembly spring 238 then the piston will not move forwards until the set dose has been fully expelled from the drug delivery device and delivered via the needle. During this action substantially no drug will flow through the intermediate opening 243. When the dose expelling from the cartridge has ended the pressure in the reservoir will drop allowing the assembly spring to move forward the piston to thereby expel drug from the reservoir via the intermediate opening 243, see FIGS. 7C and 7D. At this point both doses of drug will have been expelled during the common delivery needle.

Figure 7C:
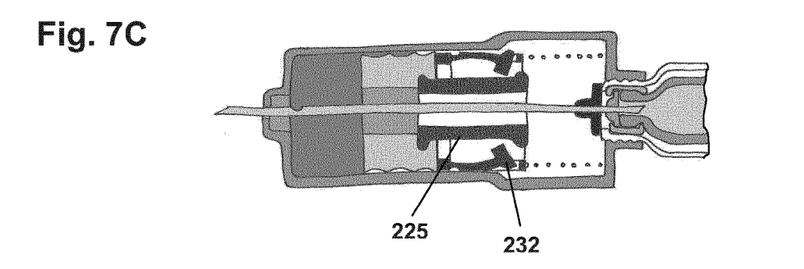
Figure 7D:
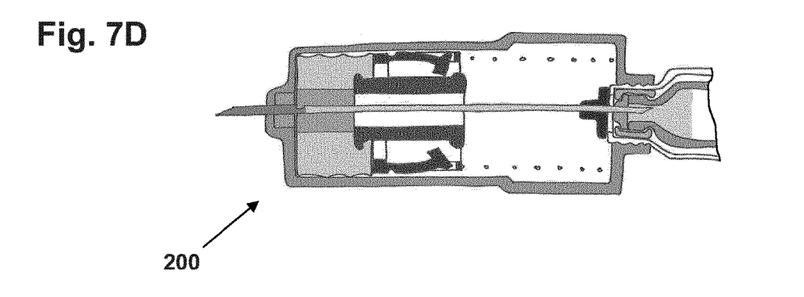

In contrast, if the force on the piston from the pressure in the reservoir generated by the device spring is lower than the force exerted on the piston from the assembly spring 238 then initially the piston will move forwards until the drug has been fully expelled from the assembly reservoir and delivered via the needle after which the dose will be expelled from the cartridge. Indeed, this requires that drug is not allowed to flow rearwards from the assembly reservoir and into the cartridge via the intermediate opening, however, as a spring-driven drug delivery device in most cases comprises a unidirectional coupling preventing the piston rod from being pushed back (e.g. as in FlexTouch® from Novo Nordisk), this is not a problem. Thus, when the drug expelling from the reservoir has ended the pressure in the reservoir will drop allowing the device spring to move forward the piston to thereby expel the set drug dose from the cartridge via the needle. Alternatively, the flow conduits of the delivery assembly could be provided with valves controlling the flow direction.

During this action substantially no drug will flow through the intermediate opening 243. When the dose expelling from the cartridge has ended the pressure in the reservoir will drop allowing the assembly spring to move forward the piston to thereby expel drug from the reservoir via the intermediate opening 243. At this point both doses of drug will have been expelled during the common delivery needle with substantially no drug remaining in the delivery assembly.

As appears, for a system comprising in combination a delivery assembly 200 pre-filled with a first drug and a drug delivery device 260 filled with a second drug the components (e.g. spring and flow characteristics) can be designed to either expel the first or the second drug first. Indeed, it may also be possible to design the system to deliver the drugs substantially at the same time. Depending on the nature of the two drugs and their formulations the order in which they are injected may influence the pharmacokinetics, e.g. blood uptake rate.

Figure 8:
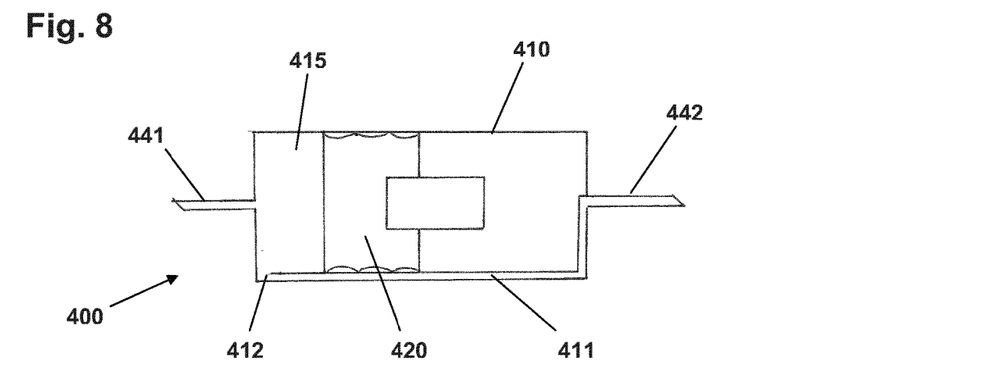
FIG. 8 shows a third embodiment of a pre-filled delivery assembly.

FIG. 8 shows schematically a third embodiment of a pre-filled delivery assembly 400 comprising a polymeric housing 410, an axially displaceable piston 420, and a drive assembly (not shown but corresponding to the above-described drive assembly 230). When the piston is arranged in its initial position a reservoir 415 is formed between the piston and the housing, the reservoir being filled with a liquid drug formulation. The housing is provided with a distal hollow needle 441 in fluid communication with the reservoir, a proximal hollow needle 442 adapted to engage a cartridge septum of a drug delivery device, and a conduit 411 formed in the wall of the housing and providing a fluid communication between the proximal needle and the reservoir, the conduit having an opening 412 at the distal-most end of the reservoir. The reservoir is provided to the user with the reservoir sealed, e.g. by sealing the needle ends by appropriate means to be removed when the assembly is taken out of its protective packaging prior to use.

In a situation of use, the third embodiment works in substantially the same way as the first embodiment when the single hollow needle of the latter has been moved forward, the difference being that the fluid communication between the cartridge of a drug delivery device and the assembly reservoir is provided via the conduit 411 and not the displaceable hollow needle 240. In a further embodiment (not shown) the assembly may be provided with manually releasable locking means.

The above-disclosed exemplary embodiments may be modified and provided with additional features to further improve user-friendliness. For example, although a piston in its distal position would indicate that the assembly had been used, a dedicated indicator may be provided showing whether or not the assembly has been actuated, e.g. a visual indicator changing colour. For example, the housing may be provided with a window showing a first colour when the assembly is in its initial state and a second colour when the assembly has been actuated and the piston has been moved to its distal position, e.g. by arranging a colour marking on the retaining member which is moved axially during actuation. To indicate that the assembly has been actuated and/or that the reservoir has been emptied the assembly may be provided with means producing one or two audible "click" sounds.

The delivery assembly may also be provided with a slideable needle guard covering the distal needle in the initial state, the needle guard being pushed proximally when the assembly is placed against a skin surface. The needle guard may be spring-biased such that it automatically is moved distally to cover the distal needle when the assembly is withdrawn from the skin surface. The needle guard could also be used to provide a lock such that the assembly cannot be released until the guard has been pushed proximally. For a design corresponding to the FIG. 6 embodiment this would allow a user to perform an "air shot", i.e. to purge air from the needle before inserting the distal needle subcutaneously. In an integrated system the axial movement of the needle guard could be used to release the drive mechanism of the drug delivery device.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery assembly, comprising:
   a housing,
   a piston axially displaceable in the housing from an initial position,
   a variable volume reservoir formed by the housing and the piston and in an initial state containing a fluid drug,
   an exterior fluid inlet arranged in or configured to be arranged in fluid communication with the reservoir,
   a fluid outlet arranged in or configured to be arranged in fluid communication with the reservoir,
   biasing means configured for moving the piston forwards, and
   releasable retaining means configured for retaining the biasing means in an energized state,
   wherein the piston comprises a fluid conduit in flow communication with the exterior fluid inlet, the piston being moveable from the initial position in which there is no fluid communication between the fluid conduit and the fluid outlet and to a connected position in which a direct fluid communication is provided between the fluid outlet and the fluid conduit and thereby between the exterior fluid inlet and the fluid outlet,
   whereby the biasing means in the energized state is allowed to move the piston forwards to expel fluid drug from the reservoir when the retaining means is released.

2. A drug delivery assembly as in claim 1, wherein the biasing means is configured to be actuated from an initial state to the energized state by a user operation.

3. A drug delivery assembly as in claim 2 configured to be attached to a drug delivery device, the drug delivery assembly further comprising:
   first coupling means,
   the drug delivery device comprising:

a second reservoir containing a second fluid drug, and
second coupling means configured for attachment to the first coupling means, wherein, when the first and second coupling means are attached to each other, the exterior fluid inlet is arranged in fluid communication with the second reservoir and the biasing means is actuated from the initial state to the energized state.

4. A drug delivery assembly as in claim 1, wherein:
the fluid outlet has an initial state in which there is no fluid communication between the fluid outlet and the reservoir, and an actuated state in which there is fluid communication between the fluid outlet and the reservoir, thereby allowing the biasing means in the energized state to move the piston forwards to expel the fluid drug from the reservoir through the fluid outlet, and
the fluid inlet has an initial state in which there is no fluid communication between the exterior fluid inlet and the reservoir, and an actuated state in which there is fluid communication between the exterior fluid inlet and the fluid outlet.

5. A drug delivery assembly as in claim 4, wherein:
the releasable retaining means comprises a needle penetrable area, and
the fluid outlet is in the form of a distal hollow needle axially displaceable between an initial position in which there is no fluid communication between the fluid outlet and the reservoir, and an actuated position in which the distal hollow needle is arranged through the needle penetrable area and thereby in fluid communication with the reservoir, whereby the biasing means in the energized state is allowed to move the piston forwards to expel the fluid drug from the reservoir through the distal hollow needle.

6. A drug delivery assembly as in claim 5, wherein:
a proximal portion of the distal hollow needle in its actuated position projects into the reservoir,
the piston comprises a needle penetrable area, and
the exterior fluid inlet is in the form of a proximal hollow needle having a distal portion arranged in the fluid piston conduit and being in flow communication therewith as the piston is moved axially from its initial position to its connected position in which the proximal portion of the distal hollow needle is arranged through the piston needle penetrable area and thereby in flow communication with the proximal hollow needle,
whereby a fluid communication is provided between the distal hollow needle and the proximal hollow needle via the fluid conduit.

7. A medical assembly comprising a drug delivery assembly as defined in claim 1 and a drug delivery device, the drug delivery assembly further comprising:
first coupling means,
the drug delivery device comprising:
a second reservoir containing a second fluid drug,
an expelling assembly configured for expelling a dose of the second fluid drug from the second reservoir, and
second coupling means configured for attachment to the first coupling means,
wherein, when the first and second coupling means are attached to each other, the exterior fluid inlet is arranged in fluid communication with the second reservoir.

* * * * *